United States Patent [19]

Grizzuti et al.

[11] Patent Number: 5,385,735

[45] Date of Patent: Jan. 31, 1995

[54] SEMDURAMICIN PREMIX

[75] Inventors: Antonio Grizzuti, Old Lyme; Robert J. Lloyd, Mystic, both of Conn.

[73] Assignee: Pfizer Inc., New York, N.Y.

[21] Appl. No.: 50,154

[22] Filed: Apr. 27, 1993

Related U.S. Application Data

[63] Continuation of Ser. No. 614,365, Nov. 16, 1990, abandoned.

[51] Int. Cl.$^6$ ............................................. A23K 1/165
[52] U.S. Cl. .................................. 424/442; 424/438; 424/439
[58] Field of Search ............... 424/442, 473, 438, 472, 424/439

[56] References Cited

U.S. PATENT DOCUMENTS

| | | | |
|---|---|---|---|
| 3,846,380 | 11/1976 | Fujimoto et al. | 424/70 |
| 3,947,586 | 3/1976 | Messersmith | 424/115 |
| 4,311,710 | 1/1982 | Clinton | 424/330 |
| 4,659,713 | 4/1987 | Hass | 514/249 |
| 4,797,275 | 11/1989 | Brooks et al. | 424/78 |
| 4,804,680 | 2/1989 | Goudie et al. | 514/460 |
| 4,804,680 | 2/1989 | Goudie et al. | 514/460 |
| 4,855,365 | 8/1989 | Yamamoto et al. | 528/328 |
| 5,126,142 | 6/1992 | Ayer et al. | 424/473 |
| 5,204,099 | 4/1993 | Barbier et al. | 528/328 |

FOREIGN PATENT DOCUMENTS

| | | |
|---|---|---|
| 0060680 | 9/1982 | European Pat. Off. |
| 0171628 | 2/1985 | European Pat. Off. |
| 0272119 | 6/1988 | European Pat. Off. |
| 55-79315 | 6/1980 | Japan ............ 424/70 |
| 1030297 | 5/1966 | United Kingdom |
| 1572114 | 7/1980 | United Kingdom |

OTHER PUBLICATIONS

Stauber, D. and R. Beutel, "Determination and Control of the Dusting Potential of Feed Premixes," Fresenius Z. Anal. Chem. (318, No. 7, 522–24, 1984).

Larrabee, Wallace L., "Microingredient Premixing," Feed Manufacturing Technology III, American Feed Industry Association, Inc., 1985; Chapter 25, pp. 242–245.

*Primary Examiner*—Thurman K. Page
*Assistant Examiner*—William E. Benston, Jr.
*Attorney, Agent, or Firm*—Peter C. Richardson; Gregg C. Benson; Robert T. Ronau

[57] ABSTRACT

An animal premix having improved levels of flowability and dustiness. The premix comprises about 2% to about 10% Semduramicin or its pharmaceutically acceptable cationic salts thereof, about 0.5% to about 50% Semduramicin degradation reducing stabilizer, about 40% to about 80% diluent, about 5% to about 50% density-increasing bulking agent, about 2% to about 10% dust controlling oil and about 0.25% to about 5% flowability enhancing glidant selected from the group consisting of sodium aluminosilicate and silicon dioxide. The invention is also directed to an animal feed containing the above described premix and a method of treating coccidial infections in an animal by administering that animal feed to an animal.

9 Claims, No Drawings

SEMDURAMICIN PREMIX

CROSS-REFERENCE TO RELATED APPLICATIONS

This application is a continuation of copending International Application No. PCT/US91/07498, filed Oct. 17, 1991, entitled "Semduramicin Premix" which is a continuation of U.S. application Ser. No. 07/614,365, filed Nov. 16, 1990, entitled "Semduramicin Premix" (now abandoned).

TECHNICAL FIELD

The field of art to which this invention pertains is animal premixes and particularly, Semduramicin premixes.

BACKGROUND OF THE INVENTION

Many animal drugs are administered by admixture with the animal feed. Typically, to facilitate a uniform drugfeed mixture a drug-feed premix is prepared because of the very low concentration of drug to feed used. The concentrated drug premix is added to and mixed through batches of feed.

Premixes are characterized by a variety of associated properties such as stability, flowability, and dustiness. Typical premixes represent a compromise of the above properties, as for example, an increase in flowability may adversely affect the dustiness of the premix.

Although there are a variety of premixes there is a continual search in this field of art for premixes that exhibit an improved mix of properties.

SUMMARY OF THE INVENTION

This invention is directed to an animal premix having improved levels of flowability and dustiness. The premix comprises about 2% to about 10% Semduramicin or its pharmaceutically acceptable cationic salts thereof, about 0.5% to about 50% Semduramicin degradation reducing stabilizer, about 40% to about 80% diluent, about 5% to about 50% density-increasing bulking agent, about 2% to about 10% dust controlling oil and about 0.25% to about 5% flowability enhancing glidant selected from the group consisting of sodium aluminosilicate and silicon dioxide.

The invention is also directed to an animal feed containing the above described premix and a method of treating coccidial infections in an animal by administering that animal feed to an animal.

Other features and advantages will be apparent from the specification and claims which describe an embodiment of this invention.

DETAILED DESCRIPTION OF THE INVENTION

This invention is directed to a premix for Semduramicin (i.e. UK-81,689; an antibiotic) or pharmaceutically acceptable salts thereof (hereinafter referred to as Semduramicin. Preferred cationic salts are the sodium, potassium and ammonium salts. An especially preferred salt is the sodium salt. Semduramicin and its production are described in U.S. Pat. No. 4,804,680 the disclosure of which is hereby incorporated by reference. Semduramicin is active against a variety of microorganisms and is effective in controlling coccidiosis, enteritis and swine dysentery as well as being effective in promotion of growth and/or improving efficiency of feed utilization in swine and ruminants.

Any amount of Semduramicin may be used in the premix that provides the desired efficacy, for the above described applications, when the premix is mixed with feed and fed to the animal. However, typically, the Semduramicin will be present in an amount from about 2 to 10% by weight of total premix. (Where used herein, the "%" symbol is meant to define percent by weight.) The preferred amount is 5 to 7% by weight. These amounts have been shown to be efficacious when administered to animals in the conventional feedmix of about 1 pound premix to 1 ton feed. The especially preferred use level in chicken feed is generally in the range of 15 to 128 ppm. A typical Semduramicin particle size is about 5 to about 100 micron.

Typically a fine particle stabilizer (e.g. about 0.1mm to about 0.8 mm) that is effective in substantially reducing the degrade%ion (e.g. hydrolysis) of Semduramicin is added to the premix. Monovalent basic or neutral salts, for example sodium carbonate, sodium sulfate, ammonium hydroxide, ammonium carbonate, potassium carbonate and sodium phosphate are effective. Preferably sodium carbonate, sodium sulfate or sodium chloride is used. It is believed that the presence of the salt reduces the solubility of the Semduramicin (when present as a salt) through the common ion effect. In addition, materials that increase the alkalinity of the medium appear to increase the stability of the drug (e.g. sodium carbonate). Any amount of stabilizer may be used that is effective in stabilizing the Semduramicin. However, typically about 0.5% to about 50% stabilizer is added to the premix. Actually little advantage in stabilization is achieved with levels above about 10%, and high levels of stabilizer may lead to insufficient quantities of other components. Below about 0.5% the desired stability is typically not achieved. Preferably about 3% to about 6% stabilizer is added to the premix.

In order to achieve the desired predetermined premix concentration, a carrier (i.e. diluent) is typically used as a component of the premix. Typically the particle size is about 0.1 to about 0.9 mm. The desired premix concentration of Semduramicin depends on the desired rate of addition of premix to finished feed. A diluent is typically an edible substance used to mix with and reduce the concentration of nutrients and/or additives to make them more acceptable to animals, safer to use, and more capable of being mixed uniformly in a feed. Exemplary diluents are plant byproducts however other suitable diluents include vermiculite, almond shells, rapeseed meal and limestone. The term by-products refers to secondary products that are produced in plant processing in addition to the principle product. Generally this means low cost, low nutritional, but edible materials. Preferred plant by-products are grain by-products and vegetable by-products. Preferable grain byproducts diluent are soybean based, rice based, wheat based, and corn based. Especially preferred diluents are soybean mill run, soybean meal, soybean hulls, soybean grits, rice hulls, rice bran, rice husks, wheat bran, wheat middlings, wheat meal, wheat germ, corn cob, corn meal, corn gluten, corn cob grits and corn germ meal. Typically about 40% to about 80% diluent is used. However it is preferred that about 40% to about 60% diluent is used because below about 40% an undesirable quantity of the below described bulking agent may be required and above 60% the premix density may be too low. It is especially preferred that about 45% to about 55% diluent is used.

An amount of fine particle bulking agent (e.g. about 0.1 mm to about 0.9 mm) effective provide the premix with bulk density of about 30 to about 50 lbs/ft$^3$ is added to the premix. Because of the low density of for example, the diluent, the bulking agent increases the density to the desired commercial level. Typical bulking agents have a density of about 2.5 g/ml to about 3.0 g/ml. Exemplary bulking agents are inert, high density materials (e.g. inert minerals, salts). Preferred bulking agents are limestone, sodium carbonate, kaolin, bentonite, oyster shells and sodium sulfate. Typically about 5% to about 50% bulking is added to the premix, however it is preferred to add about 30% to about 40% bulking agent because below about 30% the premix density may be too low.

An amount of oil effective to control dust is added to the premix. Generally it is preferred to have a dust (e.g. fine dry particulate matter) level that results in a safe, comfortable human environment during transferal of the premix. In this invention it is desired to reduce the levels of, in particular, Semduramicin dust. It is preferred to reduce the levels of Semduramicin dust to less than or equal to about 100 micrograms per membrane and especially preferred to reduce the levels of Semduramicin dust to less than or equal to about 25 micrograms per membrane. These levels are measured according to a standard dustiness test described below (prior to the Example section). Any oil may be used that is effective in achieving the desired dust levels and does not deleteriously effect other desired premix characteristics. Exemplary oils are petroleum oils ( e.g. mineral oils) and plant oils. In particular plant oils such as babassu oil, canola oil, castor oil, cocoa butter, coconut oil, corn oil, cotton seed oil, linseed oil, mustard oil, neem oil, niger-seed oil, oiticica oil, olive oil, palm oil, palm-kernel oil, peanut oil, perilla oil, poppy-seed oil, rapeseed oil, safflower oil, sesame oil, soybean oil, sunflower-seed oil, tung oil and wheat-germ oil may be used. Preferably mineral, soybean or rapeseed oil is used.

Preferably a mineral oil having a density between about 0.7 grams per milliliter (g/ml) and about 1.0 g/ml is used. It is preferred that a low density mineral oil is used when sodium carbonate is used as either the bulking agent or the stabilizer because this improves flowability. By low density is meant from about 0.7 g/ml to about 0.87 g/ml. It is also preferred that a high density mineral oil is used when limestone is used as a bulking agent because this improves flowability. By high density is meant greater than about 0.87 g/ml to less than or equal to about 1 g/ml. Preferably about 2% to about 10% oil is used because below about 2% oil the level of dust may be undesirable and above about 10% oil the flowability may be adversely effected (e.g. an undesirable amount of glidant (described below) may be necessary). It is especially preferred that about 5% to about 6.5% oil is used.

An amount of glidant effective to achieve the desired flowability, (greater than or equal to about 0.12 pounds per second per square inch), is added to the premix. This flowability level is determined according to a simple standard test described just prior to the Examples. Exemplary glidants are sodium aluminosilicate and silicon dioxide; however sodium aluminosilicate is preferred as it provides better flowability. A preferred form of silicon dioxide is colloidal silicon dioxide, which is submicroscopic fumed silica. It is light, non-gritty amorphous powder. A preferred form of sodium aluminosilicate is a hydrate having a particle size less than about 150 micron. Preferably about 0.25% to about 5% glidant is used as below about 0.25% the flowability may not be sufficient and about 5% no additional advantage is gained, although more could be used without deleterious effect. It is especially preferred that about 2% to about 3% glidant is used. In addition, it is preferred that if about 0.25% to about 2% glidant is used, that less than about 6.5% oil is used because that provides a better flow rate.

Some of the above ingredients inherently serve dual functions. Some components can function as a stabilizer and bulking agent (e.g. sodium carbonate). In the above description if a particular ingredient inherently performs more than one function the percentages are effected in the following manner. For a multi-use component, its percent in the formulation is added to each specific use, when totaling a percentage of a specific ingredient category. For example, if sodium carbonate is used at a 20% level, 20% would be considered as part .of the total amount of stabilizer required and 20% would also be considered as contributing toward the total amount of bulking agent required.

The premixes of this invention may be made by any procedure that provides a premix having the desired properties of flow, bulk density, efficacy, stability, dust control and non-caking. However typically the solid ingredients (except for glidant) are mixed together and then the oil and glidant are mixed in, in succession. It is preferred that the glidant is added last as this facilitates the desired flowability described above. It is especially preferred that the carrier, bulking agent, and stabilizer are mixed together with one-half of the oil. The drug is then added, followed by the remainder of the oil and the glidant.

Typically these premixes are added to feed which is then feed to the animals requiring the Semduramicin. In general about 0.5 to about 2 lb. of premix is used for 1 ton of feed. Preferably about 1 lb. of premix is used for 1 ton of feed. The feeds used are those which are useful for the animals that Semduramicin is an effective antibacterial or growth stimulating agent (e.g. swine, chickens).

Flowability levels as described herein are determined by reference to a standard test. The test comprises the flow of the premix through a funnel. The data measured in terms of pounds per seconds per square inches. The funnel used was constructed from stainless steel and had no welds or obstructions in the funnel path. The interior of the funnel was polished to a smooth finish. The funnel comprised a cylindrical portion 2.5 inches in diameter six inches long. The cylindrical portion converged over a distance of 2.25 inches to an interior diameter of 0.6 inch. A cylindrical portion having a diameter of 0.6 inch extended from the converging funnel portion for a distance of 1 inch.

The flowability test procedure follows. A sample of premix was placed into the metal funnel described above while keeping the bottom end closed using a dry finger. Using a stopwatch, the time required for the premix to completely flow through the funnel was measured. The stopwatch was started simultaneously with the removal of the finger from the funnel's bottom. The stopwatch was stopped when the powder flow from the funnel was completed. The density (unpacked) was determined by flowing the premix into a graduated cylinder using the above funnel. The premix's volume was read from the graduated cylinder.

Dustiness levels as described herein are determined by reference to a standard test. The dust is generated from the premix sample to be tested in a commercially available dust testing equipment (Heubach Dustmeter available from Heubach Engineering GmbH located in Germany). The generated dust was transported onto a filter membrane via an air stream. The content of active ingredient in the dust collected on the membrane was determined quantitatively by a suitable method. In brief the dust test apparatus comprised a rotating drum, of about two liters volume, into which the premix was placed. The rotating drum, at the downstream end, was in fluid communication with the bottom of a 1000 ml flask via a connection pipe approximately 9 inches long which fed through a hole in the bottom of the flask. The top of the flask was in fluid communication with a filter box of 17 cm$^2$ surface area. A suitable vacuum pump was connected to the upstream end-of the filter box.

The dustiness test procedure follows. The premix sample was placed in the dust generating drum. The vacuum air flow rate was set at 4 liters/minute. The rotating drum was set for 30 revolutions per minute and the drum motor and vacuum pump were turned on for 5 minutes. After five minutes the test apparatus was automatically turned off. The filter membrane was removed from the filter holder and the drug was dissolved and assayed. Examples 1-9 detail data that shows the premix invention has satisfactory flowability and dustiness levels (according to the above described parameters). Examples 10-18 illustrate other premixes that did not have satisfactory levels of flowability and dustiness.

EXAMPLE 1

A batch of medicated animal feed premix was prepared using the procedure described below.

The proportions of drug and excipients used for this batch are:

Semduramicin Sodium 5.64%
Rice Hulls 48.86%
Limestone (calcium carbonate) 33.0%
Sodium Carbonate 4.0%
High Viscosity Mineral Oil 6.5%
Sodium Aluminosilicate 2.0%

Manufacturing Procedure. The Procedure used for making the batches is as follows:

1. The CARRIER (rice hulls) was placed into a 2-liter beaker. The OIL was slowly added to the carrier in the beaker (using low pressure spray bottle). The carrier and oil were thoroughly mixed using a mechanical mixer (WAB model Turbula) for 10 minutes.
2. The BULKING AGENT (limestone), STABILIZER (sodium carbonate) and DRUG were added to the contents in the beaker from Step 1. The bulking agent, stabilizer, and drug were thoroughly mixed with the carrier and oil from Step 1 using a mechanical mixer (WAB model Turbula) for 15 minutes.
3. The GLIDANT was added to the mixture of carrier, oil, bulking agent, stabilizer, and drug from Step 2. This mixture, now containing all drug and excipients, was thoroughly mixed using a mechanical mixer (WAB model Turbula) for 10 minutes.
4. The completed medicated animal feed premix was placed into an appropriately sized bottle labeled with formulation and lot numbers. The flowability of the premix was determined using the funnel test (described elsewhere in this document). FLOWABILITY (metal funnel, lb/sec/in$^2$): 0.141 (initial) HEUBACH DUSTINESS VALUE (μg drug/membrane): not determined The following Example premixes (2-19) were prepared in an analogous fashion to the premix preparation used in Example 1.

| | |
|---|---|
| Semduramicin sodium | 5.45% |
| Rice Hulls | 53.8% |
| Limestone (calcium carbonate) | 32.3% |
| Sodium Carbonate | 3.56% |
| High Viscosity Mineral Oil | 3.96% |
| Colloidal silicon dioxide | 0.99% |
| FLOWABILITY (metal funnel, lb/sec/in$^2$): 0.153 (initial) | |
| HEUBACH DUSTINESS VALUE (μg drug/membrane): 72 | |

| | |
|---|---|
| Semduramicin Sodium | 5.5% |
| Rice Hulls | 50.2% |
| Limestone (calcium carbonate) | 32.8% |
| Sodium Carbonate | 4.0% |
| High Viscosity Mineral Oil | 6.0% |
| Sodium Aluminosilicate | 1.5% |
| FLOWABILITY (metal funnel, lb/sec/in$^2$): 0.154 (initial) | |
| HEUBACH DUSTINIESS VALUE (μg drug/membrane): 0.20 | |

| | |
|---|---|
| Semduramicin Sodium | 5.5% |
| Rice Hulls | 49.7% |
| Limestone (calcium carbonate) | 32.5% |
| Sodium Carbonate | 3.9% |
| High Viscosity Mineral Oil | 5.9% |
| Sodium Aluminosilicate | 2.5% |
| FLOWABILITY (metal funnel, lb/sec/in$^2$): 0.165 (initial) | |
| HEUBACH DUSTINESS VALUE (μg drug/membrane): <0.1 | |

| | |
|---|---|
| Semduramicin Sodium | 5.5% |
| Rice Hulls | 51.3% |
| Limestone (calcium carbonate) | 33.5% |
| Sodium Carbonate | 4.1% |
| High viscosity Mineral Oil | 4.1% |
| Sodium Aluminosilicate | 1.5% |
| FLOWABILITY (metal funnel, lb/sec/in$^2$): 0.177 (initial) | |
| HEUBACH DUSTINESS VALUE (μg drug/membrane): 35.8 | |

| | |
|---|---|
| Semduramicin Sodium | 5.5% |
| Rice Hulls | 50.5% |
| Limestone (calcium carbonate) | 33.0% |
| Sodium Carbonate | 4.0% |
| High Viscosity Mineral Oil | 5.0% |
| Sodium Aluminosilicate | 2.0% |
| FLOWABILITY (metal funnel, lb/sec/in$^2$): 0.161 (initial) | |
| HEUBACH DUSTINESS VALUE (μg drug membrane): 17.3 | |

| | |
|---|---|
| Semduramicin Sodium | 5.45% |

| | |
|---|---|
| -continued | |
| Rice Hulls | 53.8% |
| Sodium Carbonate | 35.8% |
| Light Mineral oil | 3.96% |
| Colloidal silicon dioxide | 0.99% |
| FLOWABILITY (metal funnel, lb./sec/in$^2$): 0.145 (initial) | |
| HEUBACH DUSTINESS VALUE (μg drug/membrane): 92 | |

| | |
|---|---|
| Semduramicin Sodium | 5.45% |
| Rice Hulls | 53.8% |
| Limestone (calcium carbonate) | 32.3% |
| Sodium Carbonate | 3.56% |
| High Viscosity Mineral Oil | 3.96% |
| Sodium Aluminosilicate | 0.99% |
| FLOWABILITY (metal funnel, lb/sec/in$^2$): 0.176 (initial) | |
| HEUBACH DUSTINESS VALUE (μg drug/membrane): 19 | |

| | |
|---|---|
| Semduramicin sodium | 5.45% |
| Rice Hulls | 53.8% |
| Sodium Carbonate | 35.8% |
| Light Mineral Oil | 3.96% |
| Colloidal silicon dioxide | 0.99% |
| FLOWABILITY (metal funnel, lb/sec/in$^2$): 0.173 (initial) | |
| HEUBACH DUSTINESS VALUE (μg drug/membrane): 51 | |

| | |
|---|---|
| Semduramicin Sodium | 5.5% |
| Soybean Millrun | 85.5% |
| Sodium Carbonate | 4.0% |
| High Viscosity Mineral Oil | 4.0% |
| Sodium Aluminosilicate | 1.0% |
| FLOWABILITY (metal funnel lb/sec/in$^2$): 0.112 (1-week) | |
| HEUBACH DUSTINESS VALUE (μg drug/membrane): not determined | |

| | |
|---|---|
| Semduramicin Sodium | 5.64% |
| Rice Hulls | 48.36% |
| Limestone (calcium carbonate) | 33.0% |
| Sodium Carbonate | 4.0% |
| High Viscosity Mineral Oil | 7.0% |
| Sodium Aluminosilicate | 2.0% |
| Flowability (metal funnel, lb/sec/in$^2$): no flow | |
| HEUBACH DUSTINESS VALUE (μg drug/membrane): not determined | |

| | |
|---|---|
| Semduramicin Sodium | 5.5% |
| Rice Hulls | 56.7% |
| Limestone (calcium carbonate) | 34.0% |
| Sodium Carbonate | 3.78% |
| FLOWABILITY (metal funnel, lb/sec/in$^2$): 0.158 (3-day) | |
| HEUBACH DUSTINESS VALUE (μg drug/membrane): 2890 | |

| | |
|---|---|
| Semduramicin Sodium | 5.5% |
| Rice Hulls | 55.5% |
| Limestone (calcium carbonate) | 33.3% |
| Sodium Carbonate | 3.7% |
| Light Mineral Oil | 2.0 |
| FLOWABILITY (metal funnel, lb/sec/in$^2$): 0.105 (3-day) | |
| HEUBACH DUSTINESS VALUE (μg drug/membrane): 610 | |

| | |
|---|---|
| Semduramicin Sodium | 5.5% |
| Rice Hulls | 53.1% |
| Limestone (calcium carbonate) | 31.86% |
| Sodium Carbonate | 3.54% |
| Light Mineral Oil | 6.0% |
| FLOWABILITY (metal funnel, lb/sec/in$^2$): no flow initial | |
| HEUBACH DUSTINESS VALUE (μg drug/membrane): <0.1 | |

| | |
|---|---|
| Semduramicin Sodium | 5.5% |
| Rice Hulls | 55.5% |
| Limestone (calcium carbonate) | 33.3% |
| Sodium Carbonate | 3.7% |
| High Viscosity Mineral Oil | 2.0% |
| FLOWABILITY (metal funnel, lb/sec/in$^2$): 0.168 (3-day | |
| HEUBACH DUSTINESS VALUE (μg drug/membrane): 720 | |

| | |
|---|---|
| Semduramicin Sodium | 5.5% |
| Rice Hulls | 53.1% |
| Limestone (calcium carbonate) | 31.86% |
| Sodium Carbonate | 3.54% |
| High Viscosity Mineral Oil | 6.0% |
| FLOWABILITY (metal funnel, lb/sec/in$^2$): no flow (initial) | |
| HEUBACH DUSTINESS VALUE (μg drug/membrane): <0.1 | |

| | |
|---|---|
| Semduramicin Sodium | 5.5% |
| Rice Hulls | 51.9% |
| Limestone (calcium carbonate) | 31.14% |
| Sodium Carbonate | 3.46% |
| High Viscosity Mineral Oil | 8.0% |
| FLOWABILITY (metal funnel, lb/sec/in$^2$): no flow (initial) | |
| HEUBACH DUSTINESS VALUE (μg drug/membrane): <0.1 | |

| | |
|---|---|
| Semduramicin Sodium | 5.5% |
| Rice Hulls | 50.8% |
| Limestone (calcium carbonate) | 33.2% |
| Sodium Carbonate | 4.0% |
| High Viscosity Mineral Oil | 4.0% |
| Sodium Aluminosilicate | 2.5% |
| FLOWABILITY (metal funnel, lb/sec/in$^2$): 0.170 (initial | |
| HEUBACH DUSTINESS VALUE (μg drug/membrane): 164 | |

It should be understood that the invention is not limited to the particular embodiments described herein, but that various changes and modifications may be made without departing from the spirit and scope of this novel concept as defined by the following claims.

It is claimed:

1. A Semduramicin animal premix comprising:

a. About 2 weight % to about 10 weight % Semduramicin or a pharmaceutically acceptable cationic salt thereof;
b. about 0.5 weight % to about 50 weight % Semduramicin degradation reducing Stabilizer;
c. about 40 weight % to about 80 weight % diluent;
d. about 5 weight % to about 50 weight % density increasing bulking agent;
e. about 2 weight % to about 10 weight % dust controlling oil; and
f. about 0.25 weight % to about 5 weight % flowability enhancing glidant selected from the group consisting of sodium aluminosilicate and silicon dioxide.

2. A premix as recited in claim 1 wherein said stabilizer is a salt selected from the group consisting of monovalent basic and neutral salts; said diluent is grain by-products; said bulking agent is selected from the group consisting of limestone and sodium carbonate; and said oil is mineral oil.

3. The premix as recited in claim 2 wherein said stabilizer is sodium carbonate; said diluent is rice hulls; said bulking agent is sodium carbonate; said oil is low density oil and said glidant is sodium aluminosilicate.

4. The premix as recited in claim 3 wherein said premix contains about 30 weight % to about 40 weight % sodium carbonate; about 45 weight % to about 55 weight % diluent; about 4 weight % to about 6.5 weight % oil; and about 1 weight % glidant.

5. The premix as recited in claim 2 wherein said stabilizer is sodium carbonate; said diluent is rice hulls; said bulking agent is limestone; said oil is high density oil; and said glidant is sodium aluminosilicate.

6. The premix as recited in claim 5 wherein said premix contains about 3 weight % to about 6 weight % stabilizer; about 45 weight % to about 55 weight % diluent; about 30 weight % to about 40 weight % bulking agent; about weight % to about 6.5 weight % oil and about 2 weight % to about 3 weight % glidant.

7. An animal feed comprising an antibacterial effective amount of the premix of claim 1 and animal feed.

8. The animal feed as recited in claim 7 comprising about 1 pound of the premix of claim 1 per 1 ton of animal feed.

9. A method of treating bacterial infections in an animal by administering an anticoccidial effective amount of the animal feed of claim 8 to said animal.

* * * * *